US00PP33639P2

(12) United States Plant Patent
Kraan

(10) Patent No.: US PP33,639 P2
(45) Date of Patent: Nov. 16, 2021

(54) ***SORBARIA* PLANT NAMED 'BOCOCOT'**

(50) Latin Name: *Sorbaria sorbifolia*
Varietal Denomination: Bococot

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), part interest; KOLSTER BV, Boskoop (NL), part interest ( * ) Notice: Subject to any disclaimer, the term of this patent is extended or adjusted under 35 U.S.C. 154(b) by 0 days.

(21) Appl. No.: 17/223,599

(22) Filed: Apr. 6, 2021

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson
(74) *Attorney, Agent, or Firm* — Penny J. Aguirre

(57) ABSTRACT

A new cultivar of *Sorbaria sorbifolia* plant named 'Bococot' that is characterized by its compact, dense and consistent plant habit, its floriferous blooming habit in summer, its foliage that is deep pink-red in color, and its fruits that are greyed-red in color.

2 Drawing Sheets

Botanical classification: *Sorbaria sorbifolia.*
Variety denomination: 'Bococot'.

BACKGROUND OF THE INVENTION

The present invention relates to a new and distinct cultivar of *Sorbaria sorbifolia* and will be referred to hereafter by its cultivar name, 'Bococot'. 'Bococot' is a new cultivar of false spirea, a shrub grown for use as a landscape plant.

The new *Sorbaria* arose from a breeding program conducted by the Inventor at a nursery in Boskoop, The Netherlands. The objective of the breeding program was to develop new *Sorbaria* cultivars with dense and compact plant habits, new foliage colors, and good flowering properties.

The new *Sorbaria* originated by open pollination in June of 2014 of *Sorbaria sorbifolia* 'Sem' (U.S. Plant Pat. No. 16,336) as the female parent. There were numerous plants of unnamed and unpatented plants of *Sorbaria sorbifolia* planted in the area. The male parent is therefore unknown. 'Bococot' was selected as a single unique plant from the resulting seedlings in 2016 (seedling reference no. 1601-01) with final selection for introduction made in 2019 after a propagation trial.

Asexual propagation of the new cultivar was first accomplished by the Inventor using stem cuttings in summer of 2018 in Boskoop, The Netherlands. Asexual propagation by stem cuttings has determined that the characteristics of 'Bococot' are stable and reproduced true to type in successive generations.

SUMMARY OF THE INVENTION

The following traits have been repeatedly observed and represent the characteristics of the new cultivar. These attributes in combination distinguish 'Bococot' as a unique cultivar of *Sorbaria.*

1. 'Bococot' exhibits a compact, dense and consistent plant habit.
2. 'Bococot' exhibits a floriferous blooming habit in summer.
3. 'Bococot' exhibits young foliage that is deep pink-red in color.
4. 'Bococot' exhibits fruits that are greyed-red in color.

The female parent plant of 'Bococot', 'Sem' differs from 'Bococot' in having a shorter plant height, young foliage that is lighter in color and more grey-orange in color, a less floriferous blooming habit, fruit that is more brown in color, and a more vigorous spreading habit. 'Bococot' can be compared to the *Sorbaria sorbifolia* cultivar 'Levgreen' (U.S. Plant Pat. No. 31,202). 'Levgreen' differs from 'Bococot' in having a smaller plant size, mature foliage that is bright green and tinged with bronze in summer, and a very sparse blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Bloomin Easy Plants, Acorn Farms, Greenleaf Nursery, Greenland Gare Centre, Van Belle Young Plants, Progress Plants, Gertens, Bron and Sons Nursery, Floral Daily, and Nursery Management magazine,

BRIEF DESCRIPTION OF THE DRAWINGS

The accompanying color photographs illustrate the overall appearance and distinct characteristics of the new *Sor-*

*baria*. The photographs were taken of a 5-year-old plant of 'Bococot' as field grown in Boskoop, The Netherlands.

Figure 1:
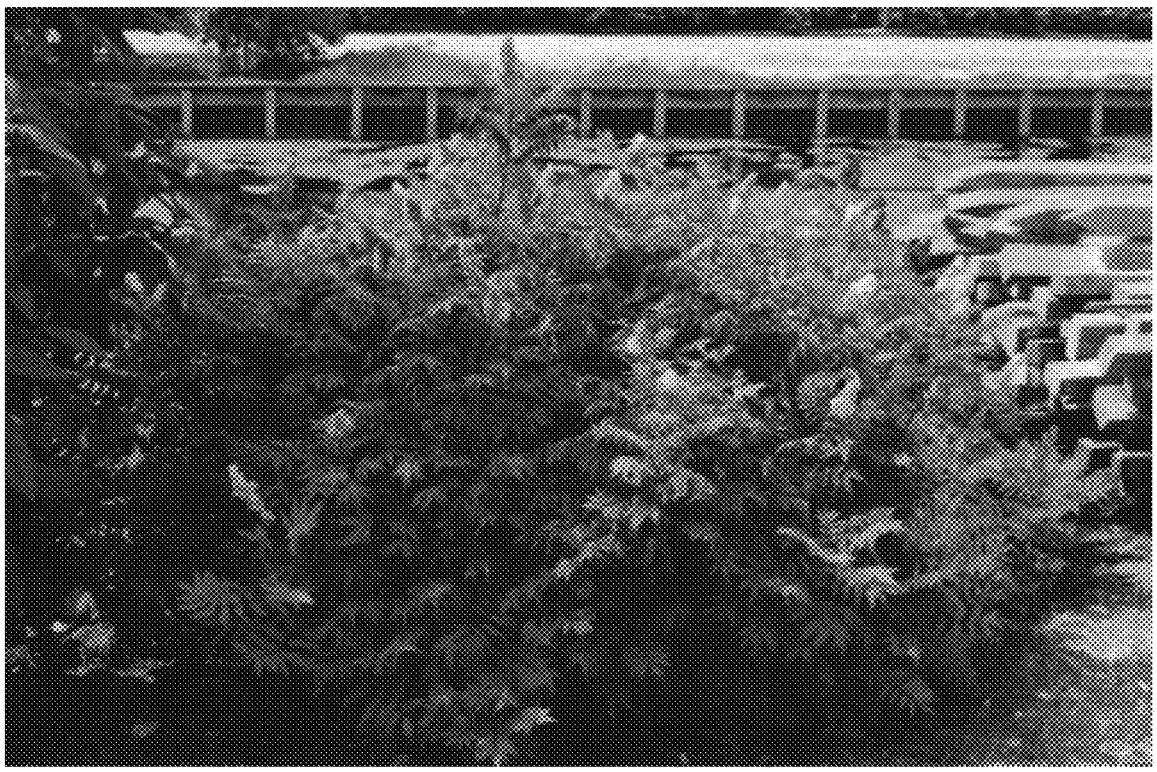

The photograph in FIG. 1 illustrates the overall appearance of the plant habit of 'Bococot'.

Figure 2:
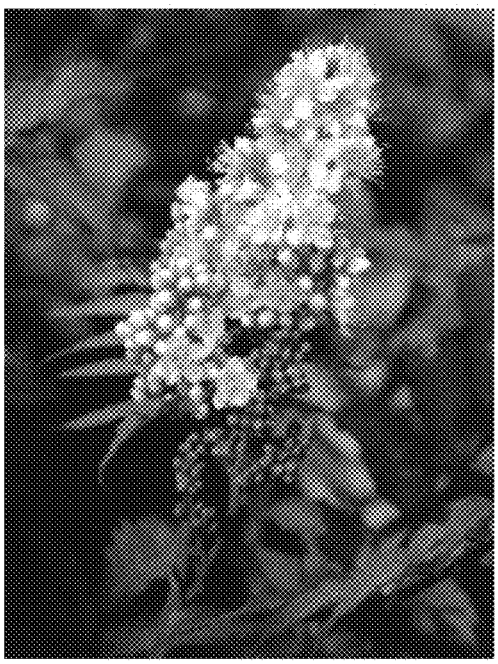

The photograph in FIG. 2 provides a close-up view of an inflorescence of 'Bococot'.

Figure 3:
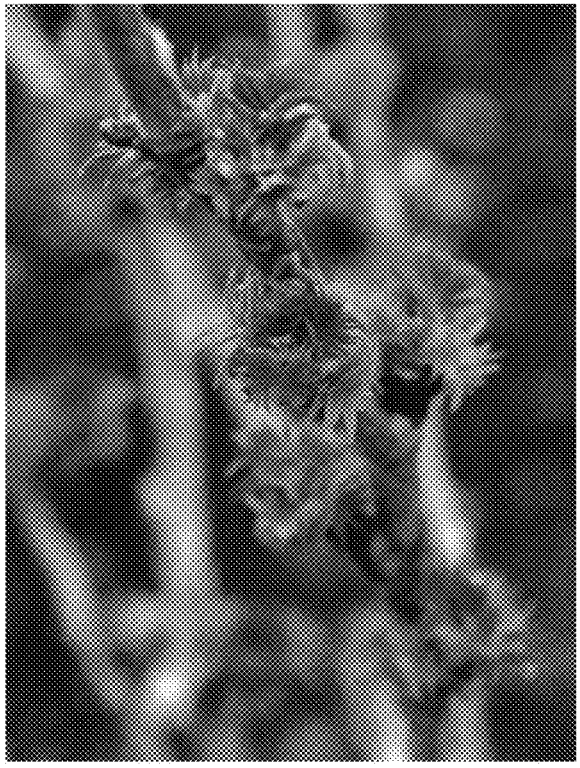

The photograph in FIG. 3 provides a view of the young foliage of 'Bococot'.

Figure 4:
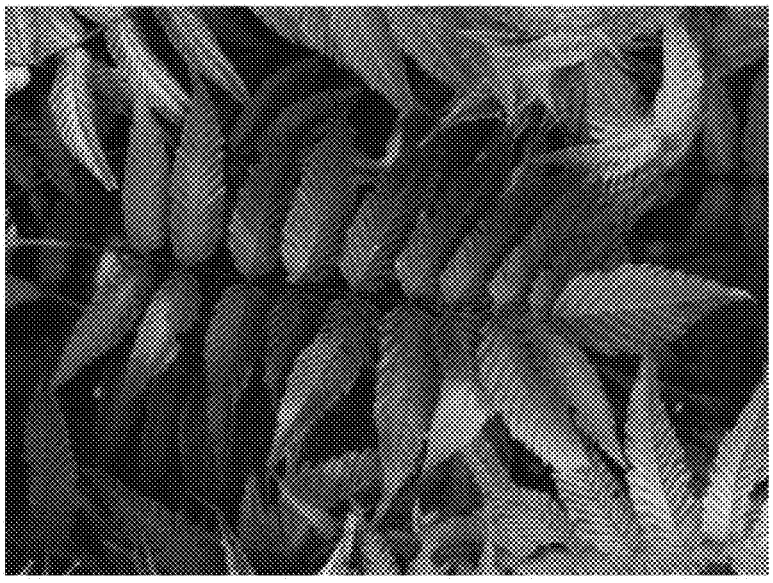

The photograph in FIG. 4 provides a view of the mature foliage of 'Bococot'.

The colors in the photographs are as close as possible with the digital photography techniques utilized and the color values cited in the detailed botanical description accurately describe the colors of the new *Sorbaria*.

DETAILED BOTANICAL DESCRIPTION

The following is a detailed description of five-year-old plants of the new *Sorbaria* as fieldgrown in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 4 weeks in July to early August in The Netherlands.

*Plant type*.—Deciduous shrub, perennial.

*Plant habit*.—Compact, dense, and broadly spreading.

*Height and spread*.—Average of 1.5 m in height and 2 m spread as a mature plant in the landscape.

*Hardiness*.—U.S.D.A. Zones 3 to 9.

*Diseases and pests*.—No resistance or susceptibility to diseases or pests has been observed.

*Root description*.—Fibrous, slightly to moderately outward spreading by underground rhizomes.

*Propagation*.—Stem cuttings.

*Root development*.—An average of 5 weeks for root development and a young rooted plant is produced in about 3 months.

*Growth rate*.—Moderate to high.

Stem description:

*Stem strength*.—Strong.

*Stem shape*.—Rounded

*Stem size*.—Average of 39.9 cm in length and 5 mm in width, base stems 1 cm in width.

*Stem surface*.—Young and mature stems are matte and glabrous.

*Stem color*.—Young; 183B, mature; 144B, tinged 183B to 183D, internode color 144B, older bark; 199C and 199D.

*Stem aspect*.—Average of 55° from main branch (varying between 50° and 60°).

*Internode length*.—Average of 2.3 cm.

*Stem quantity*.—Average of 41 main branches, 200 lateral branches.

Foliage description:

*Leaf shape*.—Oblong to slightly elliptic.

*Leaf division*.—Compound.

*Leaf aspect*.—Slightly revolute.

*Leaf arrangement*.—Alternate.

*Leaf*.—Petiolate.

*Leaflet quantity*.—Average of 18 leaflets per leaf.

*Leaflet shape*.—Lanceolate.

*Leaflet base*.—Broadly acute.

*Leaflet apex*.—Long and narrowly apiculate.

*Leaflet fragrance*.—None.

*Leaflet venation*.—Pinnate, veins furrowed, upper surface; 144A, lower surface 144D.

*Leaflet margins*.—Biserrate, medium undulation, unlobed.

*Leaflet surface*.—Both surfaces smooth, glabrous, nonrugose, matte.

*Leaf/leaflet size*.—Leaf; average of 19.1 cm in length and 12.4 cm in width, leaflet; 6.1 cm in length, 1.7 cm in width.

*Leaflet color*.—Young upper surface; 53C to 53D, changing to N34C, then changing to 37A to 22B, margins 154A to 154B, later changing to 11B to 11D before maturing, young lower surface; 53B, changing to N34C to N45D, then changing to 35A to 35B to 25C, margins 154A to 154B, later changing to 11B to 11D before maturing, mature upper surface; NN137C, mature lower surface; 137C and 147B.

*Petioles*.—Average of 17.7 cm in length (from base to base of top of leaflet) and 2 mm in diameter, both sides smooth and glabrous, upper surface matte, lower surface slightly glossy, strong, color; upper surface 146B, slightly to strongly tinged 183A, lower surface 146D.

*Stipules*.—At the base of each leaf are 2 leafy stipules, narrow elliptic in shape, average of 1.2 cm in length, 3 mm in width, narrow apiculate apex, narrow cuneate base, both surfaces glabrous and slightly glossy.

Inflorescence description:

*Inflorescence type*.—Terminal panicle.

*Inflorescence size*.—Average of 5.2 cm in diameter and 12.1 cm in height.

*Flower quantity*.—Average of 280 per inflorescence, 7,000 flowers and buds per plant.

*Lastingness of inflorescence*.—Individual flowers average of one week, self-cleaning.

*Flower type*.—Single.

*Flower habit*.—Low to moderate.

*Flower aspect*.—Rotate, upright to slightly outward.

*Flower fragrance*.—Moderate, unpleasant.

*Flower buds*.—Ovate in shape, average of 4 mm in length and 3 mm in diameter, color; NN155D, immature sepals 144B, tinged 172B.

*Flower size*.—Average of 7 mm in depth, 1.1 cm in diameter.

*Peduncle*.—Average of 11.6 cm in length, 1.75 mm in diameter, held in a vertical angle, strong, smooth, matte and glabrous surface, color; 143C, sunny side tinged 183A.

*Pedicels*.—Average of 3.5 mm in length, 1 mm in diameter, held in an average angle of 45°, strong, smooth, matte and glabrous surface, color; 144B.

*Calyx*.—Rotate, average of 2.5 mm in length, 4.5 mm in diameter.

*Sepals*.—Rotate, 5, 1 whorl, 2.5 mm in length, 1.8 mm in width, apex acute, ovate, reflexed in shape, entire margins; both surfaces matte, smooth, glabrous, when opening upper surface 145C, when opening lower surface 144B, tinged 172B, when fully open upper and lower surface 150B, tinged 173B.

*Petals*.—Rotate, 5 per flower, 1 whorl, unfused, 4.5 mm in length, 3 mm in width, ovate, moderately concave in shape, emarginate tip curled backwards, cuneate base, entire margins, smooth, glabrous, slightly velvety, non-rugose, matte, color; upper and lower surface when opening and fully open NN155D.

Reproductive organs:

*Gynoecium*.—Pistil; 5, average of 3 mm in length, style; 2.7 cm in length, NN155A, stigma; 3 mm in length and diameter, club-shaped, 155A in color, ovary; 150D in color.

*Androecium*.—Stamens; 32 (varying between 30 and 35), filaments; NN155A in color, average of 5 mm in length, anthers; dorsifixed, double broadly ovate in shape, 0.5 mm in length, 0.4 mm in width, 155A, pollen; low in quantity, 156D in color.

*Fruit*.—Average of 7,000 per plant, 6 mm in length, 4 mm in diameter, smooth surface, moderately covered with very short glandular hairs, surface color 178A, not edible, fruit consisting of 5 fused, cylindrical seed pods.

*Seed*.—Average of 10 per fruit, 1.5 mm in length, 0.5 mm in diameter, smooth, glabrous and N200A in color.

It is claimed:

1. A new and distinct cultivar of *Sorbaria* plant named 'Bococot' as herein illustrated and described.

* * * * *